United States Patent [19]

Van Albert et al.

[11] Patent Number: 4,794,549
[45] Date of Patent: Dec. 27, 1988

[54] EXCITO-REPELLENCY TEST SYSTEM

[75] Inventors: Stephen A. Van Albert; Jaime M. Lee; Donald R. Roberts, all of Montgomery, Md.

[73] Assignee: The United States of America as represented by the Secretary of the Army, Washington, D.C.

[21] Appl. No.: 910,914

[22] Filed: Sep. 19, 1986

[51] Int. Cl.⁴ .................. G06M 7/00; G01V 9/04; G08B 23/00
[52] U.S. Cl. .................... 364/551.01; 377/6; 73/866; 250/221; 340/573
[58] Field of Search ............... 364/550, 551; 377/1, 377/6, 16, 17, 24, 24.2, 53; 250/221, 222.1, 222.2; 340/555–557, 573; 73/866

[56] References Cited

U.S. PATENT DOCUMENTS

| | | | |
|---|---|---|---|
| 3,040,980 | 6/1962 | Mann et al. | 377/6 |
| 3,439,358 | 4/1969 | Salmons | 377/6 X |
| 3,494,329 | 2/1970 | Frieberger et al. | 377/6 X |
| 3,540,413 | 11/1970 | Castaigne | 377/6 X |
| 3,633,001 | 1/1972 | Vajnovszky | 377/6 |
| 4,009,389 | 2/1977 | Lindholm | 340/555 X |
| 4,095,092 | 6/1978 | Neff | 377/6 |
| 4,179,839 | 12/1979 | Salotti et al. | 377/6 X |
| 4,272,762 | 6/1981 | Geller et al. | 250/221 X |
| 4,278,878 | 7/1981 | Kato | 377/45 X |
| 4,748,860 | 6/1988 | Butler et al. | 73/866 |

Primary Examiner—Gary Chin
Assistant Examiner—Joseph L. Dixon
Attorney, Agent, or Firm—Peter A. Taucher; Gail S. Soderling

[57] ABSTRACT

An apparatus for measuring insecticide activity. A chamber holds a plurality of insects and a quantity of the insecticide to be tested. An exit is formed in the chamber so that insects escaping from the chamber pass through a detector to generate a signal. The signals are compared to other signals generated by the other insects passing the detector to determine the repellency of the insecticides.

4 Claims, 2 Drawing Sheets

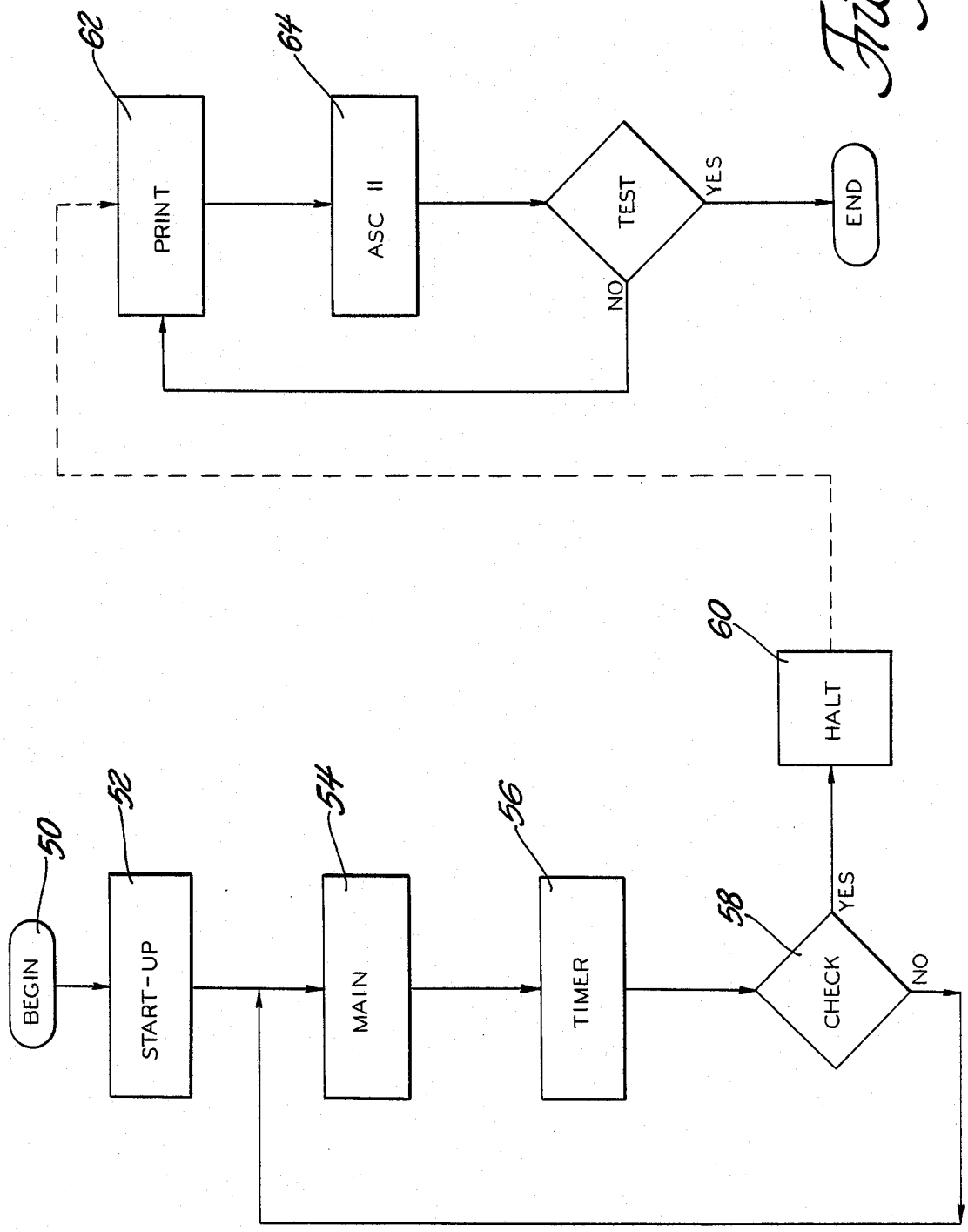

EXCITO-REPELLENCY TEST SYSTEM

GOVERNMENT INTEREST

The invention described herein may be manufactured, used, and licensed by or for the Government for governmental purposes without payment to us of any royalty thereon.

BACKGROUND OF THE INVENTION

1. Field of the Invention

In one aspect this invention relates to a device suitable for testing the reaction of insects to insecticides residues.

In a further aspect, this invention relates to a device suitable for counting the movement of insects past a predetermined point.

2. Description of Related Art

Various counting devices have been shown in the art relating to the counting of various objects past a predetermined point. For example, U.S. Pat. No. 3,633,001 discloses an apparatus which can measure the effect of psychostimulants on laboratory animals by measuring the intermittent contacts of the animal's feet on the floor of a cage which has been specially prepared to react to the passage of the animal as it moves about the cage. Pulses generated by the animal are amplified and the pulses are counted and recorded. The number of pulses counted in a given time are taken as an indication of the activity of the psychostimulants on the animal.

Another counting device is shown by U.S. Pat. No. 4,333,096 which shows a seed planter. This patent shows a device where seeds passing a point while being dispensed through a chute are counted and in the case of multiple dispensing chutes, the deviation between the chutes is calculated and signaled to a warning device.

The types, varieties and uses of insecticides have proliferated since the discovery of the insecticidal properties of DDT. Today the insecticide industry comprises millions of dollars and is repsonsible for protecting a substantial portion of the total crops grown for food and forage in the developed farming economies. Further, insecticides are responsible for controlling insects which transmit various diseases e.g. malaria. The continued improvement of the health and well being of the world's population depends on the wise and effective use of insecticides.

Serious problems have developed because of the appearance of insects which are resistant to many types of insecticides. This is particularly true of medically important insects. Most tropical and semitropical countries have some form of insect control program for the purpose of controlling the mosquitoes which vector malaria and other insect-borne diseases. The questions of insecticide resistance and avoidance of treated surfaces is of paramount importance.

Over the years, there is evidence that the behavioral resistance or avoidance of insecticides is as important to the control of insect disease vectors as the physiological resistance commonly discussed. For mosquitoes, this was first proposed in 1964. Similar behavioral patterns effecting the behavioral resistance of insect vectors to insecticides has been reported for most of the medically important species throughout the world. One of the problems in relating the data is the lack of a consistent study method for determining behavoral avoidance (behavorial resistance) of the insects to insecticide treated surfaces.

Indeed the World Resources Institute has published reports acknowledging that the most critical constraint to fully implementing resistance monitoring is the lack of technical knowledge and suitable techniques. There are no presently existing techniques which enable a quick inexpensive measurement of the resistance or reactions of insects to new or existing insecticides. The development of new methods would have benefits such as monitoring the resistance of insects to a given insecticide allowing the change of an insecticide before a substantial percentage of an insect population has developed a behavioral resistance pattern.

Also, an improved monitoring system would allow a method of testing various insecticides in order to determine the relative effectiveness and repellency of the compounds in order to choose between compounds or to know when it would be desirable to change insecticides in order to continue to obtain control. The device of the present invention and method of using same is designed to provide a system which has enhanced portability, automation, standardization, quantification and reliability.

SUMMARY OF THE INVENTION

A system according to the present invention which measures the activity of mosquitoes according to their reaction to an insecticide includes a chamber which can hold a number of insects to be tested. The chamber has a sample holder which holds a sample of the insecticide to be tested at a constant position in the chamber and an exit is formed in one wall of the chamber to provide an escape path for the insects to leave the chamber. A photosensitive detector is located so that escaping insects move directly into the path of the detector as they exit the chamber. As the insect passes through the detector it will produce an electrical impulse which can be sensed and used as a measure of the number of insects exiting the chamber. Using a computing means, the impulses can be related to each other and to other insecticides as a function of time and concentration so as to measure the relative effectiveness of the various insecticides. The data being analyzed, can be related to a given standard number of insects per given time unit or compared to other tests.

DESCRIPTION OF THE DRAWINGS

In the accompanying drawing:

FIG. 2 is a flow chart for the counting and calculation sequence of one embodiment of this invention.

DETAILED DESCRIPTION OF THE PREFERRED EMBODIMENTS

Figure 1:
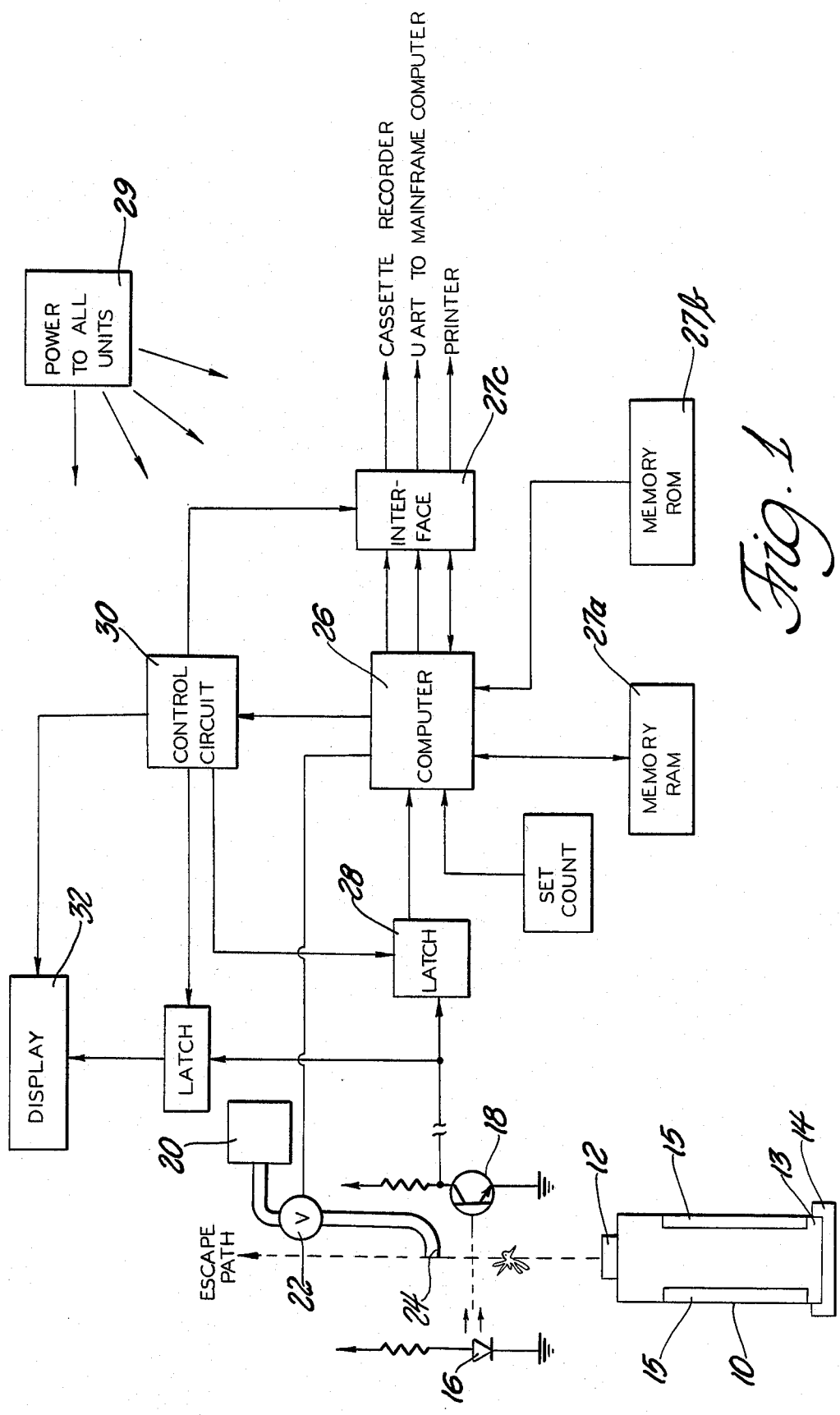
FIG. 1 is a block diagram of one system constructed according to this invention.

Referring to the accompanying drawing and initially to FIG. 1, an insect chamber 10 is formed with an exit 12 for insects at one end of the chamber. The exit will be formed so that insects exiting the chamber will pass a photodetector which is located adjacent the exit 12. As shown, at the opposite end of the chamber, an entrance 13 is formed and sealed with a closure 14. The entrance is designed so that insects to be tested are introduced into the chamber in order to test the insects repulsion to a given insecticide. As shown, insecticide treated papers line the inside of the chamber (10) where the desired number of insects are introduced. Actually insecticide can be located at various locations on or within the chamber depending on how the test is to be performed. However, locating the insecticide as far from the exit as possible ensures that the insects will not become trapped in the chamber in a position where the insect has to go past the insecticide in order to escape. The chamber is configured so as to hold the standard insecticide test samples coated on a sheet of paper commonly used by insecticide researchers.

The detector is located so that insects which are exiting the chamber will pass directly through the detection device. As shown, the detector comprises a light source such as a light emitting diode 16 and a receptor, such as a phototransistor, 18 which will register changes in illumination falling on the receptor When an insect exits the chamber it will momentarily decrease the light falling on the photoreceptor indicating an insect has passed. The resulting electrical impulse change will be sent to the computer for processing in accordance with a predefined relationship which depends on the insect and repellent being tested. A more detailed description is set forth below.

In order to count each insect once and avoid repeats, a mechanism for cleaning the exit and to prevent multiple exits is desirable. One mechanism for accomplishing this task is shown in FIG. 1. A source of compressed gas 20 such as air is connected to a valve 22 which is in turn connected to a nozzle 24 located at the exit 12 of the chamber. The valve 22 is electrically connected to the computer and when an insect passes through the sensor, the computer will open the valve allowing a gust of gas to blow across the exit. This will have two desirable effects, first, the insect will be blown away from the mouth of the exit so it does not crawl back and forth through the exit giving false readings and second, insects will generally not exit until the gust of gas stops so each insect will be counted individually. This ensures a more accurate count and better data from which to draw inferences. The nozzle 24 is located in close proximity to the exit 12 so that it blows across the exit.

Only one chamber is shown for the purposes of illustration, but more than one chamber can be established and use the same computer as will be discussed below The computer 26 represents the second major portion of the present system. It is responsible for controlling the exit and valve 22 and counting the number of insects exiting the chamber as well as storing the insects counted in memory 27a. The computer also can calculate the rate at which the insects exit the chamber in order to compare the effect of an insecticide to a predetermined standard or to another chamber with a different insecticide. These and other permanent functions reside in the computer read only memory 27b. The computer and related equipment are powered by the power memory supply 29 which can be internal such as a battery or external such as an Ac to DC power supply which changes 120 V AC to 6 V DC. For use in the laboratory the power supply attached to a standard outlet will be a preferred method while the battery power supply provides a protable testing device. The exact details of the power supply will depend on the computer to be used and the power available. Also where the unit is to be used in a field environment for extended periods various battery packs may be desirable. One exmaple of of a suitable AC to DC converter employing a standard outlet would employ a 1.2 ampere 12 volt regulator, a power transistor and assorted filter capacitors and biasing resistors, which will provide an acceptable source of 6 volt current.

The interaction between the test chambers and the counter is controlled by the related circuitry shown surrounding the computer. This circuitry controls the flow of information within the system as will be discussed in greater detail below.

When a test has been completed, the computer will send its output through an interface 27c to one of a number of possible data receivers i.e., tape, printer or large computer.

OPERATION OF THE SYSTEM

The operation of the system is further understood by referring to FIG. 2 which shows a flow diagram of one system suitable for use with the apparatus of FIG. 1. In general the system is turned on 50 and and the system will go through a preprogrammed procedure 52 which as shown will check the system's components and reset the counters, read into the system any preset values from set switches, and place the system in the mode to run. The system will generally wait at this point until an activating button or switch is activated to start testing.

Once the system is activated, the system will enter the main module 54 and begin by resetting the latches 28 in the system so that data from the various testing chambers is received and recognized by the computer. As noted before, the light emitting diode 16 phototransistor 18 pair operate to detect the presence of an insect passing through the gap between them. The passage of the insect will cause a biasing of the transistor which in turn is sensed by an electrical circuit such as a dual one shot circuit which requires two sequential shots to complete the circuit's action and result in a count. The two step sequential system can provide a refractory period in the system which prevents false counting where the insect does not move rapidly through the gap. Preventing false counts is very important in gathering accurate data.

The count data passes through the control circuit 30 and is displayed on the display counter 32 as an occurrence. The data is also stored in the RAM of the computer as an increment count to the present test by the main operation 54 and can be used later in the generation of reports relating the counts from various chambers as a function of time and insecticide.

After there has been a count, the system goes to the timer sequence 56, which initiates a one second delay routine as shown. The delay can be varied depending on the insects being tested and the expected rate at which the insects would be expected to leave the chamber. A one second delay has proved a reasonable time for small flying insects such as mosquitos. After the preset delay, the system goes to the check routine which checks the time remaining in the test cycle. The initial set up can allow for presetting the time for the test or a standard test cycle can be established. If there is time remaining in the test cycle, the system recycles to the main mode and reads the results in the input from the sensors. The time, check, read loop is repeated until the check function reveals that the allotted time for the test is finished and the system passes to the halt mode 60.

As shown, the system will remain in the halt mode 62 until there is a further signal to begin printing. Then the computer will total the counts for each minute to the tape and print out the data. As shown, the Print data is first translated to ASCII format at function 64 and sent to the printer. After each block of data is written to the printer, the system tests 64 to see if there is additional incoming data which needs to be printed and will continue until there is no more incoming data and when all the data is printed, the system will stop.

We wish it to be understood that we do not desire to be limited to the exact details of construction shown and described for obvious modifications will occur to a person skilled in the art, without departing from the spirit and scope of the appended claims.

What is claimed is:

1. An apparatus for measuring the activity of insects in response to an insecticide comprising: at least one chamber for holding a plurality of insects; an insecticide sample holder which holds a quantity of the insecticide to be tested for repellency; an exit formed in the chamber so as to provide an escape path for insects to leave the chamber; a detector located near the exit formed in the chamber so that an insect traveling along the escape path will pass through the detector, the passage of the insect causing the detector to generate a signal for each insect showing the passage of one of the insects; a computer which receives the signal and processes the signal to generate data and relate it to other signals from the chamber in a predetermined relationship indicating the degree of repellency; a recorder which receives and stores the data and relationship calculated by the computer for later use and analysis; and means for cleaning an insect from the exit and delaying the passage of additional insects through the exit for a predetermined period of time the means for clearing including a source of compressed gas, a nozzle located near the exit formed in the chamber so as to direct the compressed gas across the exit, the nozzle being fluidly connected to the source of compressed gas, a valve which is opened for a predetermined time when an insect is sensed by the detector in the exit path to clear the insect from the exit and deter another insect from entering the exit for a predetermined period of time.

2. The system of claim 1 wherein the detector is a photo-sensitive detector comprising a light source which is a light emitting diode and a receptor which is a phototransistor.

3. An apparatus for measuring the activity of insects in response to an insecticide comprising: at least one chamber for holding a plurality of insects; an insecticide tested for repellency; an exit formed in the chamber so as to provide an escape path for insects to leave the chamber; a photosensitive detector having a receptor and a light source located so that an insect traveling along the escape path will pass through the photosensitive detector the passage of the insect causing the photosensitive detector to generate an electrical impulse showing the passage of an insect; a computer which receives the electrical impulse and processes the impulse to generate data and relate it to other impulses from the chamber in a predetermined relationship indicating the degree of repellency; a recorder which receives and stores the data and relationships calculated by the computer; and means for clearing an insect from the exit and delaying the passage of additional insects through the exit for a predetermined period of time the means for clearing including a source of compressed gas, a nozzle located near the exit formed in the chamber so as to direct the compressed gas across the exit, the nozzle being fluidly connected to the source of compressed gas, a valve which is opened for a predetermined time when an insect is sensed by the detector in the exit path to clear the insect from the exit and deter another insect from entering the exit for a predetermined period of time.

4. The system of claim 3 where the light source is a light emitting diode and the receptor is a phototransistor.

* * * * *